US007232829B2

(12) United States Patent
Portoghese et al.

(10) Patent No.: US 7,232,829 B2
(45) Date of Patent: Jun. 19, 2007

(54) THERAPEUTIC COMPOUNDS AND METHODS

(75) Inventors: Philip S. Portoghese, St. Paul, MN (US); Robert M. Jones, San Diego, CA (US); Shiv K. Sharma, Minneapolis, MN (US)

(73) Assignee: Regents of the University of Minnesota, St. Paul, MN (US)

( * ) Notice: Subject to any disclaimer, the term of this patent is extended or adjusted under 35 U.S.C. 154(b) by 39 days.

(21) Appl. No.: 10/473,245

(22) PCT Filed: Apr. 6, 2001

(86) PCT No.: PCT/US01/11339

§ 371 (c)(1),
(2), (4) Date: May 3, 2004

(87) PCT Pub. No.: WO02/080919

PCT Pub. Date: Oct. 17, 2002

(65) Prior Publication Data
US 2004/0242882 A1  Dec. 2, 2004

(51) Int. Cl.
A61K 31/44 (2006.01)
(52) U.S. Cl. ........................... 514/279; 546/35
(58) Field of Classification Search ............... 546/35; 514/279
See application file for complete search history.

(56) References Cited

U.S. PATENT DOCUMENTS

| 4,362,870 A | 12/1982 | Portoghese | 542/403 |
|---|---|---|---|
| 4,401,672 A | 8/1983 | Portoghese | 424/260 |
| 4,440,932 A | 4/1984 | Kotick et al. | 546/44 |
| 4,559,157 A | 12/1985 | Smith et al. | 252/90 |
| 4,608,392 A | 8/1986 | Jacquet et al. | 514/844 |
| 4,612,302 A | 9/1986 | Szabo et al. | 514/11 |
| 4,649,200 A | 3/1987 | Portoghese et al. | 546/26 |
| 4,684,620 A | 8/1987 | Hruby et al. | 514/11 |
| 4,806,556 A | 2/1989 | Portoghese | 546/44 |
| 4,816,586 A | 3/1989 | Portoghese | 544/340 |
| 4,820,508 A | 4/1989 | Wortzman | 424/59 |
| 4,853,371 A | 8/1989 | Coy et al. | 514/12 |
| 4,938,949 A | 7/1990 | Borch et al. | 424/10 |
| 4,992,478 A | 2/1991 | Geria | 514/782 |
| 5,223,507 A | 6/1993 | Dappen et al. | 514/279 |
| 5,225,417 A | 7/1993 | Dappen et al. | 514/279 |
| 5,244,904 A | 9/1993 | Nagase et al. | 514/285 |
| 5,298,622 A | 3/1994 | Portoghese et al. | 546/15 |
| 5,332,818 A | 7/1994 | Nagase et al. | 546/37 |
| 5,352,600 A | 10/1994 | Gelfand et al. | 435/194 |
| 5,352,680 A | 10/1994 | Portoghese et al. | 514/279 |
| 5,354,863 A | 10/1994 | Dappen et al. | 546/35 |
| 5,411,965 A | 5/1995 | Reid et al. | 514/279 |
| 5,436,249 A | 7/1995 | Dappen et al. | 514/279 |
| 5,457,208 A | 10/1995 | Portoghese et al. | 546/35 |
| 5,464,841 A | 11/1995 | Portoghese et al. | 514/279 |
| 5,578,725 A | 11/1996 | Portoghese et al. | 546/35 |
| 5,631,263 A | 5/1997 | Portoghese et al. | 514/279 |
| 5,886,001 A | 3/1999 | Schmidhammer | 514/279 |

FOREIGN PATENT DOCUMENTS

| EP | 0254545 | 1/1988 |
|---|---|---|
| EP | 0374756 | 6/1990 |

(Continued)

OTHER PUBLICATIONS

Lewis, Buprenorphine, (1985), PMID: 2986930.*

(Continued)

Primary Examiner—Amelia A. Owens
(74) Attorney, Agent, or Firm—Viksnins Harris & Padys PLLP

(57) ABSTRACT

The invention provides kappa receptor agonists of formula (I) and delta receptor antagonists of formula (II), wherein $R_1$–$R_6$ X and n have any of the meanings given in the specification, as well as compositions comprising them, methods for their use, and synthetic procedures and intermediates useful for their preparation.

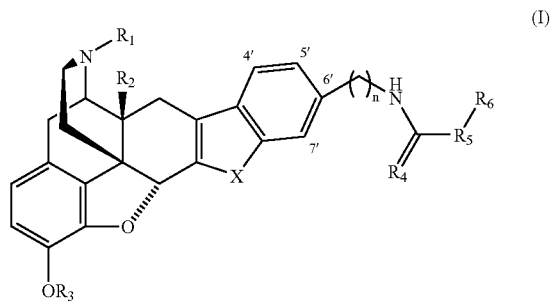

(I)

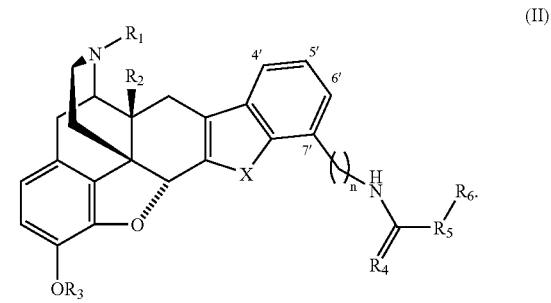

(II)

19 Claims, 5 Drawing Sheets

FOREIGN PATENT DOCUMENTS

| | | |
|---|---|---|
| EP | 0456833 A1 | 11/1991 |
| WO | WO-9407896 | 4/1994 |
| WO | WO-95/31464 | 11/1995 |
| WO | WO-96/23793 | 8/1996 |
| WO | WO-96/34005 | 10/1996 |
| WO | WO-99/18021 | 4/1999 |
| WO | WO-00/08027 | 2/2000 |

OTHER PUBLICATIONS

Bowdle, Adverse effects of opoid agonists and agonist-antagonists in anaesthesia, (1998) PMID:9747665.*

Pugsley, Antiarrhythmic effects of U-50,488H in rats subject to coronary artery occlusion, abstract, that teach U-50,488H, a selective kappa receptor agonist has no effect on arrhythmias.(1992).*

Abdelhamid, Essam E., et al., "Selective Blockage of Delta Opiod Receptors Prevents the Development of Morphine Tolerance and Dependence in Mice.", *The Journal of Pharmacology and Experimental Therapeutics*, 258, (1991),299-303.

Arakawa, K., et al., "The Immunosuppressive Effect of Opioid Receptor Antagonist on Xenogenic Mixed Lymphocyte Reaction.", *Transplantation Proceedings*, 24(2), (Apr. 1992),696-697.

Barber, A., et al., "Opiod Agonists and Antagonists: An Evaluation of Their Peripheral Actions in Inflammation", *Medicinal Research Reviews*, 12(5), (Sep. 1992),525-562.

Barlow, J. J., et al., "Structure/Activity Studies Related to 2-(3,4-Dichlorophenyl)-N-methyl-N-(2-(1-pyrrolidinyl)-1-substituted-ethyl)acetamides: A Novel Series of Potent and Selective K-Opiod Agonists", *Journal of Medicinal Chemistry*, 34(11), (Nov. 1991),3149-3158.

Bertalmio, A. J., et al., "Differentiation Between Mu and Kappa Receptor-Mediated Effects in Opioid Drug Discrimination: Apparent pA2 Analysis", *The Journal of Pharmacology and Experimental Therapeutics*, 243 (2), (Nov. 1987),591-597.

Birch, P. J., et al., "Preparation and Evaluation of Some Hydriphilic Phenylacetyl-peperazines as Peripheraly Selective k-Opiod Agonists", *Bioorganic & Medicinal Chemistry Letters*, 2, (1992),1275-1278.

Botros, S. , et al., "Opioid Agonist and Antagonist Activities of Peripherally Selective Derivatives of Naltrexamine and Oxymorphamine.", *Journal of Medicinal Chemistry*, 32(9), (Sep. 1989),2068-2071.

Brown, D. R., et al., "The Use of Quarternary Narcotic Antagonists in Opiate Research.", *Neuropharmacology*, 24(3), (Mar. 1985),181-191.

Chang, An-Chih , et al., "Arylacetamide-Derived Fluorescent Probes: Synthesis, Biological Evaluation, and Direct Fluorescent Labeling of k Opioid Receptors in Mouse Microglial Cells", *Journal of Medicinal Chemistry*, 39(8), (Apr. 12, 1996),1729-1735.

Chang, An-Chih , et al., "k Opioid receptor selective affinity labels: electrophilic benzeneacetamides as k-selective opioid antagonists", *Journal of Medicinal Chemistry*, 37(26), (Dec. 23, 1994),4490-4498.

Costello, G. F., et al., "2-(3,4-Dichlorophenyl)-N-methyl-N-(2-(1-pyrrolidinyl)-1-substituted-ethyl)actamides: The Use of Conformational Analysis in the Development of a Novel Series of Opioid K Agonists", *Journal of Medicinal Chemistry*, 34(1), (Jan. 1991),181-189.

Dhawan, B. N., et al., "Classification of Opioid Receptors", *Pharmacological Reviews*, 48(4), (Dec. 1996),567-583.

Drower, Edward J., et al., "Selective Antagonism by Naltrindole of the Antinociceptive Effects of the Delta Opioid Agonist Cyclic (D-Penicillamine2-D-Penicillamine5) Enkephalin in the Rat.", *The Journal of Pharmacology and Experimental Therapeutics*, 259, (1991),725-731.

Erez, M. , et al., "Narcotic Antagonist Potency of Bivalent Ligands which Contain B-Naltrexamine. Evidence for Bridging Between Proximal Recognition Sites.", *Journal of Medicinal Chemistry*, 25(7), (Jul. 1982),847-849.

Hjorth, S. A., et al., "Analysis of Selective Binding Epitopes for the Kappa Opioid Receptor Antagonist Nor-Binaltorphimine", *Molecular Pharmacology*, 47(6), (Jun. 1995),1089-1094.

Jaffe, Jerome H., et al., "Opioid Analgesics and Antagonists", *The Pharmacological Basis of Therapeutics, Eighth Edition*, A.G. Gilman et al., (Eds.) Peragomon Press, New York,(1990),485-521.

Jones, R. M., et al., "5'-Guanidinonaltrindole, a highly selective and potent—opioid receptor antagonist", *European Journal of Pharmacology*, 396(1), (May 12, 2000),49-52.

Jones, R. M., et al., "k-Opioid Receptors: recent advances and implications for drug design", *Curr. Opin. Drug Discuss. Dev.*, 1, (1998),175-182.

Jones, Robert M., et al., "Mutational Evidence for a Common k Antagonist binding packet in the wild-type k and mutant u[k303e] opioid receptors", *Journal of Medicinal Chemistry*, 41(25), (Dec. 3, 1998),4911-4914.

Kataoka, H. , "Novel Indolomorphinan Derivatives.", *Chemical Abstracts*, 73, Abstract No. 120798v,(1970),398.

Linner, K. M., et al., "The Delta-opioid receptor antagonist, 7-benzylspiroindanylnaltrexone, prolongs renal allograft survival in a rat model", *European Journal of Pharmacology*, 354(1), (Dec. 11, 1998),R3-R5.

Linney, I. D., et al., "Design, Synthesis, and Structure-Activity Relationships of Novel Non-Imidazole Histamine H3 Receptor Antagonists", *Journal of Medicinal Chemistry*, 43(12), (Jun. 15, 2000),2362-2370.

Martin, W. R., "Pharmacology of Opioids", *Pharmacological Reviews*, 35, (1984),283-323.

Olmsted, S. L., et al., "A Remarkable Change of Opioid Receptor Selectivity on the Attachment of a Peptidomimetic K Address Element to the Antagonist, Natrindole: 5'-(N-Alkylamidino) methyl) naltrindole Derivatives as a Novel Class of K Opioid Receptor Antagonists.", *Journal of Medicinal Chemistry*, 36(1), (Jan. 8, 1993),179-180.

Portoghese, Philip S., et al., "A Novel Opioid Receptor Site Directed Alkylating Agent with Irreversible Narcotic Antagonistic and Reversible Agonistic Activities.", *Journal of Medicinal Chemistry*, 23(3), (Mar. 1980),233-234.

Portoghese, Philip S., et al., "Application of the Message-Address Concept in the Design of Highly Potent and Selective Non-Peptide Opioid Receptor Antagonists.", *Journal of Medicinal Chemistry*, 31, (Feb. 1988),281-282.

Portoghese, Philip S., et al., "Bimorphinans as High Selective, Potent k Opioid Antagonists", *Journal of Medicinal Chemistry*, 30(2), (1987),238-239.

Portoghese, Philip S., et al., "Binaltorphimine and Norbinaltorphimine, Potent and Selective Kappa-Opioid Receptor Antagonists", *Life Sciences*, 40(13), (Mar. 30, 1987),1287-1292.

Portoghese, Philip S., et al., "Binaltorphimine-Related Bivalent Ligands and their k Opioid Receptor Antagonist Selectvity", *Journal of Medicinal Chemistry*, 31(4), (Apr. 1988),836-841.

Portoghese, Philip S., "Bivalent ligands and the message-address concept in the design of selective opioid receptor antagonists.", *Trends in Pharmacological Sciences*, 10, (Jun. 1989),230-235.

Portoghese, Philip S., et al., "Naltrindole 5'-Isothiocyanate: A Nonequilibrium Highly selective Delta Opioid Receptor Antagonist", *Journal of Medicinal Chemistry*, 33(6), (Jun. 1990),1547-1548.

Portoghese, Philip S., et al., "Naltrindole, a Highly Selective and Potent Non-Peptide Delta Opioid Receptor Antagonist", *European Journal of Pharmacology*, 146(1), (Jan. 27, 1988),185-186.

Portoghese, Philip S., et al., "Only One Pharmacophore is Required for the K Opioid Antagonist Selectivity of Norbinaltorphimine.", *Journal of Medicinal Chemistry*, 31(7), (Jul. 1988),1344-1347.

Portoghese, Philip S., et al., "Opioid antagonist activity and binding studies of regioisomeric isothiocyanate derivatives of naltrindole: evidence for .delta. receptor subtypes", *Journal of Medicinal Chemistry*, 35(22), (Oct. 30, 1992),4086-4091.

Portoghese, Philip S., et al., "Role of Spacer in Conferring Opioid Receptor Selectivity to Bivalent Ligands Related to Norbinaltorphimine.", *Journal of Medicinal Chemistry*, 34(4), (Apr. 1991),1292-1296.

Portoghese, Philip S., et al., "Structure-Activity Relationship of N17-Substituted Norbinaltorphimine Congeners. Role of the N17 Basic Group in the Interaction with a Putative Address Subsite on the k Opioid Receptor", *Journal of Medicinal Chemistry*, 37(10), (May 13, 1994),1495-1500.

Portoghese, Philip S., et al., "TENA, A Selective Kappa Opioid Receptor Antagonist.", *Life Sciences*, 36(8), (Feb. 25, 1985),801-905.

Reid, Larry D., et al., "Naltrindole, An Opioid Delta Receptor Antagonist, Blocks Cocaine-Induced Facilitation of Responding for Rewarding Brain Stimulation.", *Life Sciences*, 52(9), (1993),PL6767-71.

Rogers, H., et al., "GR94839 a k-Opioid Agonists with Limited Access to the Central Nervous System, has Antinociceptive Activity", *British Journal of Pharmacology*, 106(4), (Aug. 1992),783-789.

Shaw, J. S., et al., "ICI 204448: A k-Opioid Agonist with Limited access to the CNS", *British Journal of Pharmacology*, 96(4), (Apr. 1989),986-992.

Simon, E. J., et al., "Opioid Receptor Multiplicity: Isolation, Purification, and Chemical Characterization of Binding Sites", *In: Opiods I*, Herz, A., Ed., Springer-Verlag, Berlin, Germany,(1993),3-26.

Smith, C F., "16-Me Cyprenorphine (RX 8008M): A Potent Opioid Antagonist with some Selectivity.", *Life Sciences*, 40(3), (Jan. 19, 1987),267-274.

Sofuoglu, M., et al., "Differential Antagonism of Delta Opioid Agonists by Naltrindole and its Benzofuran Analog (NTB) in Mice: Evidence for Delta Opioid Receptor Subtypes.", *The Journal of Pharmacology and Experimental Therapeutics*, 257, (1991),676-680.

Stevens, W. C., et al., "Potent and Selective Indolomorphinan Antagonists of the Kappa-Opioid Receptor", *Journal of Medicinal Chemistry*, 43(14), (2000),2759-2769.

Takemori, A. E., et al., "Nor-Binaltorphimine, A Highly Selective Kappa-Opioid Antagonist in Analgesic and Receptor Binding Assays.", *Journal of Pharmacology and Experimental Therapeutics*, 246, (1988),255-258.

Takemori, A. E., et al., "The Irreversible Narcotic Antagonist and Reversible Agonistic Properties of the Fumaramate Methyl Ester Derivative of Naltrexone.", *European Journal of Pharmacology*, 70(4), (Apr. 9, 1981),445-451.

Ward, Susan J., et al., "Improved Assays for the Assessment of K and Properties of Opioid Ligands.", *European Journal of Pharmacology*, 85(2), (Nov. 19, 1982),163-170.

Yamamura, Mark S., et al., "Characterization of (3H)Naltrindole Binding to Delta Opioid Receptors in Rat Brain.", *Life Sciences*, 50(16), (1992),PL119-124.

\* cited by examiner

Schemes 2-6

THERAPEUTIC COMPOUNDS AND METHODS

GOVERNMENT FUNDING

The invention described herein was made with U.S. Government support under Grant Number DA01533 awarded by the National Institute on Drug Abuse. The United States Government has certain rights in the invention.

CROSS-REFERENCE TO RELATED APPLICATIONS

This application is a continuation application under 35 U.S.C. 371 of International Application No. PCT/US01/101339, filed Apr. 6, 2001 and published in English as WO 02/080919 A1 on Oct. 17, 2002, the disclosures of which is incorporated by reference herein.

BACKGROUND OF THE INVENTION

Endogenous opioid peptides are known and are involved in the mediation or modulation of a variety of mammalian physiological processes, many of which are mimicked by opiates or other non-endogenous opioid ligands. Some of the effects that have been suggested include analgesia, tolerance and dependence, appetite, renal function, gastrointestinal motility, gastric secretion, learning and memory, mental illness, epileptic seizures and other neurological disorders, cardiovascular responses, and respiratory depression, see G. T. Shearman et al. *J. Pharmacol. Exp. Ther.*, 243, 591–597, 1987.

The fact that the effects of endogenous and exogenous opioids are mediated by at least three different types of opioid receptors raises the possibility that highly selective exogenous opioid agonist or antagonist ligands might have therapeutic applications. Thus, if a ligand acts at a single opioid receptor type or subtype, the potential side effects mediated through other opioid receptor types can be minimized or eliminated.

The kappa opioid receptor is one of the three major opioid receptors that are found in the central nervous system and in the periphery, see Dhawan, B. N.; Cesselin, R.; Raghubir, R.; Reisine, T.; Bradley, P. B.; Portoghese, P. S.; Hamon, M. International Union of Pharmacology. XII. Classification of Opioid Receptors. *Pharmacol. Rev.* 1996, 48, 567–583. The precise roles of kappa receptors have not yet been established, but it appears that kappa-selective endogenous opioid peptides, such as dynorphin A, function both as neuro- and immuno-modulators.

A number of nonpeptide kappa agonists have been developed as promising potential analgesics, and some of them have found wide use as pharmacological tools in opioid research, see Jones, R. M.; Paterlini, M. G. κ-Opioid Receptors: recent advances and implications for drug design. *Curr. Opin. Drug Discuss. Dev.* 1998, 1, 175–182. Norbinaltorphimine (norBNI 1) a bivalent ligand shown in FIG. 3, which contains two naltrexone-derived pharmacophores, is a nonpeptide ligand that is highly selective and widely used as a kappa opioid receptor antagonist, see Portoghese, P. S.; Lipkowski, A. W.; Takemori, A. E. Bimorphinans as High Selective, Potent κ Opioid Antagonists. *J. Med. Chem.* 1987, 30, 238–239.

Additionally, International Patent Application PCT/US 99/18021, filed Jun. 8, 1999, reports certain kappa receptor antagonists. Data is provided for certain specific 5'-guanidinonaltrindole compounds demonstrating the compounds were found to have activity as kappa receptor antagonists.

Despite the above reports, there exists a need for kappa receptor agonists that can be used as therapeutic agents such as analgesics, or as pharmacological tools to further investigate kappa receptor binding, structure, and function. In particular, there is a need for potent and selective agonists that can be used to treat conditions associated with kappa receptor function.

SUMMARY OF THE INVENTION

Applicants have unexpectedly discovered that moving the 5'-substituent on the naltrindole compounds prepared in PCT/US 99/18021 to the 6'-position converts the compounds from kappa receptor antagonists to kappa receptor agonists. Thus, the invention provides kappa agonist compounds which provide highly selective pharmacological agonism both in vivo and in vitro at the kappa opioid receptor.

Accordingly, the invention provides a compound of formula (I):

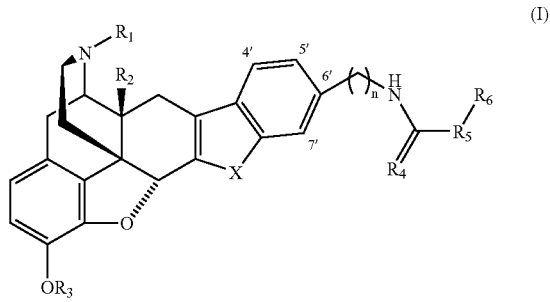

wherein $R_1$ is $(C_1-C_6)$alkyl, $(C_2-C_6)$alkenyl, $(C_2-C_6)$alkynyl, $(C_3-C_7)$cycloalkyl, $(C_5-C_7)$cycloalkenyl, $(C_3-C_6)$cycloalkyl$(C_1-C_6)$alkyl, $(C_5-C_7)$cycloalkenyl$(C_1-C_6)$alkyl, aryl, heteroaryl, aryl$(C_1-C_6)$alkyl, or heteroaryl$(C_1-C_6)$alkyl;

$R_2$ is H, OH, $(C_1-C_6)$alkoxy, $(C_1-C_6)$alkanoyloxy, $NR_aR_b$ or $SR_c$;

$R_3$ is H, aryl$(C_1-C_6)$alkyl, $(C_1-C_6)$alkyl, $(C_1-C_6)$alkanoyl, or $(C_1-C_6)$alkylC(=S);

$R_4$ is =O, =S, or =$NR_d$;

$R_d$ is H, CN, $CONH_2$, $COCF_3$, $(C_1-C_6)$alkanoyl, $(C_1-C_6)$alkyl, or $(CH_2)_pNR_eR_f$; or $R_d$ together with $R_6$ is —$(CH_2)_q$— and forms a ring;

p is 1, 2, 3, or 4;

$R_5$ is $NR_m$;

$R_6$ is H, $(C_1-C_6)$alkyl, $(C_3-C_7)$cycloalkyl, aryl, heteroaryl, aryl$(C_1-C_6)$alkyl, heteroaryl$(C_1-C_6)$alkyl, $NR_gR_h(C_1-C_6)$alkyl, or C(=$NR_j$)$NHR_k$; or when $R_4$ is =$NR_d$, $R_6$ together with $R_d$ is —$(CH_2)_q$— and forms a ring;

q is 2 or 3;

X is O, S, or NY;

Y is H, $(C_1-C_6)$alkyl, or aryl$(C_1-C_6)$alkyl;

n is 0, 1, 2, 3, or 4;

$R_a-R_c$ and $R_e-R_f$ are each independently H, $(C_1-C_6)$alkyl, $(C_1-C_6)$alkanoyl, or —C(=S)($C_1-C_6$)alkyl;

$R_g$ and $R_h$ are each independently H, $(C_1-C_6)$alkyl, $(C_1-C_6)$alkanoyl, —C(=NH)$NR_aR_b$, or —C(=S)

($C_1$–$C_6$)alkyl, or $R_g$ and $R_h$ together with the nitrogen to which they are attached are pyrrolidino, piperidino or morpholino;

$R_j$ and $R_k$ are each independently H, ($C_1$–$C_6$)alkyl, ($C_2$–$C_6$)alkenyl, ($C_2$–$C_6$)alkynyl, ($C_3$–$C_7$)cycloalkyl, ($C_3$–$C_7$)cycloalkyl($C_1$–$C_6$)alkyl, ($C_5$–$C_7$)cycloalkenylalkyl, aryl, heteroaryl, aryl($C_1$–$C_6$)alkyl, or heteroaryl ($C_1$–$C_6$)alkyl; and $R_m$ is hydrogen or ($C_1$–$C_6$)alkyl;

or a pharmaceutically acceptable salt thereof.

The invention also provides a pharmaceutical composition comprising a compound of formula (I), or a pharmaceutically acceptable salt thereof, in combination with a pharmaceutically acceptable diluent or carrier.

Additionally, the invention provides a therapeutic method for preventing or treating a pathological condition or symptom in a mammal, such as a human, wherein kappa receptor activity is implicated and agonism of kappa receptors is desired comprising administering to the mammal, an effective amount of a compound of formula (I), or a pharmaceutically acceptable salt thereof.

The invention also provides a compound of formula (I) for use in medical therapy (preferably for use in treating conditions wherein agonism of kappa receptors is indicated (e.g. for treating pain), as well as the use of a compound of formula (I) for the manufacture of a medicament for the treatment of a pathological condition or symptom in a mammal, such as a human, wherein agonism of kappa receptors is indicated (e.g. pain).

Applicants have also unexpectedly discovered that moving the 5'-substituent on the naltrindole compounds prepared in PCT/US 99/18021 to the 7'-position converts the compounds from kappa receptor antagonists to delta receptor antagonists. Thus, the invention provides delta antagonist compounds which provide highly selective pharmacological antagonism both in vivo and in vitro at the delta opioid receptor.

Accordingly, the invention provides a compound of formula (II):

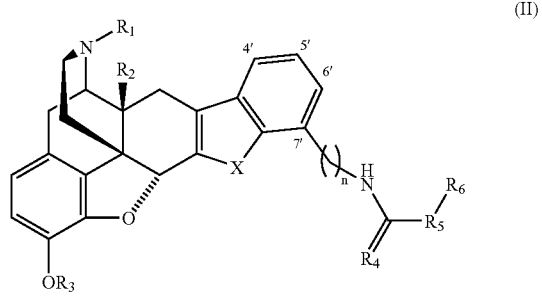

(II)

wherein $R_1$–$R_6$ and X have any of the values, specific values or preferred values described herein for the corresponding group in a compound of formula (I).

The invention also provides a pharmaceutical composition comprising a compound of formula (II), or a pharmaceutically acceptable salt thereof, in combination with a pharmaceutically acceptable diluent or carrier.

Additionally, the invention provides a therapeutic method for preventing or treating a pathological condition or symptom in a mammal, such as a human, wherein delta receptor activity is implicated and antagonism of delta receptors is desired comprising administering to the mammal, an effective amount of a compound of formula (II), or a pharmaceutically acceptable salt thereof.

The invention also provides a compound of formula (II) for use in medical therapy (preferably for use in treating conditions wherein antgonism of delta receptors is indicated), as well as the use of a compound of formula (II) for the manufacture of a medicament for the treatment of a pathological condition or symptom in a mammal, such as a human, wherein antagonism of delta receptors is indicated.

The invention also provides a method for binding a compound of formula (I) to kappa receptors, in vivo or in vitro, comprising contacting mammalian tissue comprising said receptors with an amount of a compound of formula (I) effective to bind to said receptors. Tissue comprising ligand bound kappa receptors is useful to measure the receptor selectivity of other potential therapeutic agents, or can be used as a tool to identify potential therapeutic agents for the treatment of diseases or conditions wherein kappa receptor activity is implicated and agonism of kappa receptors is desired, by contacting said agents with said ligand-receptor complexes, and measuring the extent of displacement of the ligand and/or binding of the agent (for example in a competitive binding assay).

The invention also provides a method for binding a compound of formula (II) to delta receptors, in vivo or in vitro, comprising contacting mammalian tissue comprising said receptors with an amount of a compound of formula (II) effective to bind to said receptors. Tissue comprising ligand bound delta receptors is useful to measure the receptor selectivity of other potential therapeutic agents, or can be used as a tool to identify potential therapeutic agents for the treatment of diseases or conditions wherein delta receptor activity is implicated and antagonism of delta receptors is desired, by contacting said agents with said ligand-receptor complexes, and measuring the extent of displacement of the ligand and/or binding of the agent (for example in a competitive binding assay).

Applicant has also discovered a method for preparing multi-gram quantities of the kappa antagonist GNTI 3 as its dihydrochloride salt (as well as compounds of formula (I) and formula (II)), which eliminates the need for tedious chromatographic separation. Accordingly, the invention also provides a method for preparing GNTI 3, as well as compounds of formula (I) and formula (II), as described hereinbelow.

DETAILED DESCRIPTION

Figure 1:
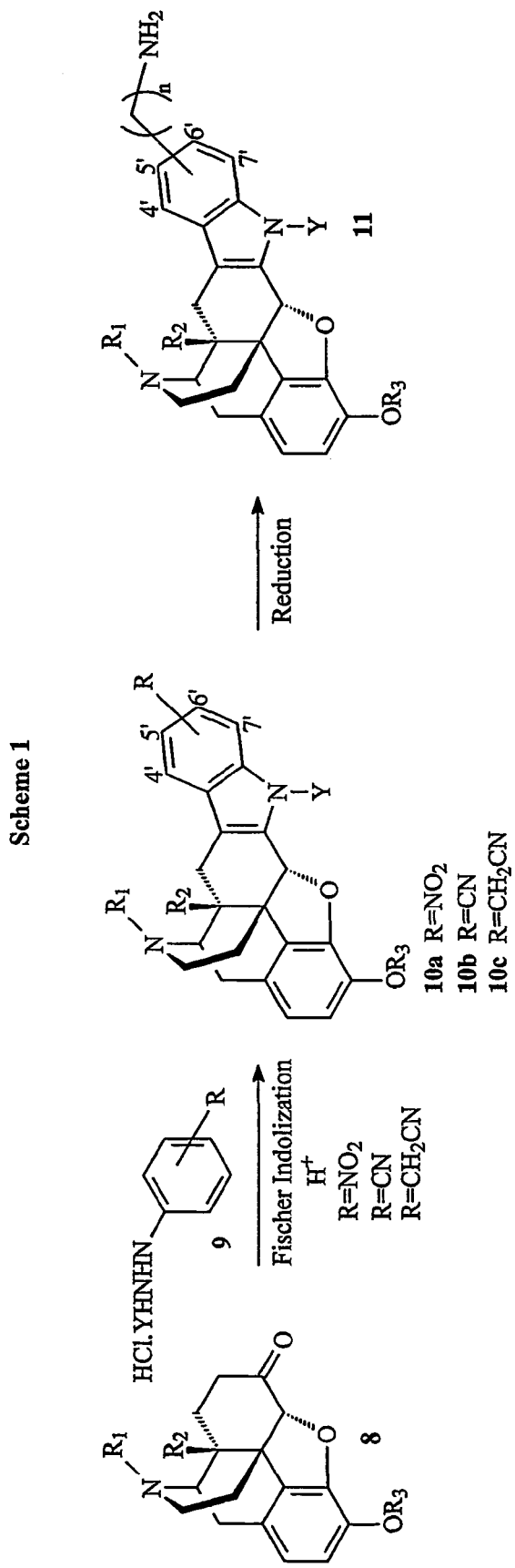
FIG. 1 Illustrates the synthesis of compounds of the invention.

Conditions wherein the kappa receptor is implicated, which can be treated by agonism of the kappa receptor are well known. For example, see Vaccarino A. L. and Kastin A.

J. Peptides, 2000, 21, 1975–2034. Such conditions include convulsions, ischemic brain damage, hypertension, AIDS, and arrhythmia.

Conditions wherein the delta receptor is implicated, which can be treated by antagonism of the delta receptor are well known. See for example Vaccarino A. L. and Kastin A. J. Peptides, 2000, 21, 1975–2034; and U.S. Pat. Nos. 4,816,586; 5,578,725; 5,411,965; 5,352,600; 5,464,841; 5,298,622; and 5,631,263. Such conditions include, for example, immunoregulatory diseases associated with a depressed autologous mixed lymphocyte response such as rheumatoid arthritis, systemic lupus erythematosis, Sjogren's Syndrome, multiple sclerosis, chronis lymphocytic leukemia, Type I diabetes, Epstein-Barr virus, and AIDS; certain viral infections including coronavirus or cytomegalovirus; cocaine use or addiction. Delta receptor antagonists are also useful as antitussive agents and to prevent the tolerance or physical dependence associated with the administration of a μ-opioid agonist.

The following definitions are used, unless otherwise described: halo is fluoro, chloro, bromo, or iodo. Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$ alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine kappa antagonist activity using the standard tests described herein, or using other similar tests which are well known in the art.

Specific values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_3-C_7)$cycloalkyl can be cyclopropyl, cyclobutyl, cyclopentyl, cyclohexyl, or cycloheptyl; $(C_3-C_7)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; halo$(C_1-C_6)$alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy$(C_1-C_6)$alkyl can be hydroxymethyl, 1-hydroxyethyl, 2-hydroxyethyl, 1-hydroxypropyl, 2-hydroxypropyl, 3hydroxypropyl, 1-hydroxybutyl, 4-hydroxybutyl, 1-hydroxypentyl, 5-hydroxypentyl, 1-hydroxyhexyl, or 6-hydroxyhexyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; and $(C_2-C_6)$alkanoyloxy can be acetoxy, propanoyloxy, butanoyloxy, isobutanoyloxy, pentanoyloxy, or hexanoyloxy; aryl can be phenyl, indenyl, or naphthyl; heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

Specifically, $R_1$ is $(C_2-C_6)$alkenyl or $(C_3-C_6)$cycloalkyl $(C_1-C_6)$alkyl. More specifically, $R_1$ is cyclopropylmethyl or allyl.

Specifically, $R_2$ is OH.

Specifically, $R_3$ is H.

Specifically, $R_4$ is $=NR_d$. More specifically, $R_4$ is $=NH$ or $=NCN$.

Specifically, $R_5$ is NH.

Specifically, $R_6$ is hydrogen, ethyl, n-butyl, 3-(dimethylamino)-propyl, or 2-pyrrolidinoethyl. More specifically, $R_6$ is H. Another specific $R_6$ is $C(=NR_j)NHR_k$.

Specifically, $R_m$ is hydrogen.

Specifically, n is 0.

Specifically, n is 1.

Specifically, X is NH.

A specific compound of the present invention is a compound of formula (I) wherein: $R_1$ is $(C_1-C_6)$alkyl, $(C_2-C_6)$alkenyl, $(C_2-C_6)$alkynyl, $(C_3-C_7)$cycloalkyl, $(C_5-C_7)$cycloalkenyl, $(C_3-C_6)$cycloalkyl$(C_1-C_6)$alkyl, $(C_5-C_7)$cycloalkenyl$(C_1-C_6)$alkyl, aryl, heteroaryl, aryl$(C_1-C_6)$alkyl, heteroaryl$(C_1-C_6)$alkyl; $R_2$ is H, OH, $(C_1-C_6)$alkoxy, $(C_1-C_6)$alkanoyloxy, $NR_aR_b$ or $SR_c$; $R_3$ is H, aryl$(C_1-C_6)$alkyl, $(C_1-C_6)$alkyl, $(C_1-C_6)$alkanoyl, or $(C_1-C_6)$alkylC$(=S)$; $R_4$ is $=O$, $=S$, $=NR_d$, wherein $R_d$ is H, CN, $CONH_2$, $COCF_3$, $(C_1-C_6)$alkanoyl, $(C_1-C_6)$alkyl, or $(CH_2)_p$ $NR_eR_f$, wherein p=1–4; $R_5$ is NH; $R_6$ is H, $(C_1-C_6)$alkyl, $(C_3-C_7)$cycloalkyl, aryl, heteroaryl, aryl$(C_1-C_6)$alkyl, heteroaryl$(C_1-C_6)$alkyl, $NR_gR_h(C_1-C_6)$alkyl, or $C(=NR_j)$ $NHR_k$; or when $R_4$ is $=N$, $R_6$ can be $-(CH_2)_q-$ and form a ring with the N of $R_4$, wherein q is 2 or 3; X is O, S, or NY, wherein Y is H $(C_1-C_6)$alkyl, or aryl$(C_1-C_6)$alkyl; n is 0, 1, 2, 3, or 4; $R_a-R_f$ are each independently H, $(C_1-C_6)$ alkyl, $(C_1-C_6)$alkanoyl, or $-C(=S)(C_1-C_6)$alkyl; $R_g$ and $R_h$ are each independently H, $(C_1-C_6)$alkyl, $(C_1-C_6)$alkanoyl, $-C(=NH)NR_aR_b$, or $-C(=S)(C_1-C_6)$alkyl, or $R_g$ and $R_h$ together with the nitrogen to which they are attached are pyrrolidino, piperidino or morpholino; and $R_j$ and $R_k$ are each independently H, $(C_1-C_6)$alkyl, $(C_2-C_6)$alkenyl, $(C_2-C_6)$alkynyl, $(C_3-C_7)$cycloalkyl; $(C_3-C_7)$cycloalkyl ($C_1$–$C_6$)alkyl, ($C_5$–$C_7$)cycloalkenylalkyl, aryl, heteroaryl, aryl($C_1$–$C_6$)alkyl, or heteroaryl($C_1$–$C_6$)alkyl; or a pharmaceutically acceptable salt thereof.

A specific compound of the invention is a compound of formula (I) wherein $R_6$ is not ($C_1$–$C_6$)alkyl when n is 1, $R_4$ is NH, and $R_5$ is NH.

A specific compound of the invention is a compound of formula (I) wherein $R_d$ together with R is —$(CH_2)_q$— and forms a ring.

A specific compound of the present invention is 6'-guanidinyl-17-cyclopropylmethyl-6,7-didehydro-4,5-á-epoxy-3,14-dihydroxyindolo[2',3':6,7]morphinan ditrifluoroacetate dihydrate.

A specific compound of the present invention is 6'-N-ethylguanidinyl-17-cyclopropylmethyl-6,7-didehydro-4,5-á-epoxy-3,14-dihydroxyindolo[2',3':6,7]morphinan ditrifluoroacetate dihydrate.

A specific compound of the present invention is 6'-N-butylguanidinyl-17-cyclopropylmethyl-6,7-didehydro-4,5-á-epoxy-3,14-dihydroxyindolo[2',3':6,7]morphinan ditrifluoroacetate dihydrate.

A specific compound of the present invention is 6'-N-butylguanidinyl-17-cyclopropylmethyl-6,7-didehydro-4,5-á-epoxy-3,14-dihydroxyindolo[2',3':6,7]morphinan ditrifluoroacetate dihydrate.

A specific compound of the present invention is 6'-N'-cyano-N-[17-(cyclopropylmethyl)-6,7-didehydro-4,5á-epoxy-3,14-dihydroxyindolo[2',3':6,7]morphinian]-guanidine.

A specific compound of the present invention is 6'-N-cyano-N'-[3-(dimethylaminopropyl)]-N"-[17-(cyclopropylmethyl)-6,7-didehydro-4,5á-epoxy-3,14-dihydroxyindolo[2',3':6,7]morphinian]-guanidine.

A specific compound of the present invention is 6'-N-cyano-N'-[2-(1-aminoethylpyrrolidine)]-N"-[17-(cyclopropylmethyl)-6,7-didehydro-4,5á-epoxy-3,14-dihydroxyindolo[2',3':6,7]morphinian]-guanidine.

A specific compound of the present invention is 7'-guanidinyl-17-cyclopropylmethyl-6,7-didehydro-4,5-á-epoxy-3,14-dihydroxyindolo[2',3':6,7]morphinan ditrifluoroacetate dihydrate.

A specific compound of the present invention is 7'-N-ethylguanidinyl-17-cyclopropylmethyl-6,7-didehydro-4,5-á-epoxy-3,14-dihydroxyindolo[2',3':6,7]morphinan ditrifluoroacetate dihydrate.

A specific compound of the present invention is 7'-N-butylguanidinyl-17-cyclopropylmethyl-6,7-didehydro-4,5-á-epoxy-3,14-dihydroxyindolo[2',3':6,7]morphinan ditrifluoroacetate dihydrate.

A specific compound of the present invention is 7'-N-butylguanidinyl-17-cyclopropylmethyl-6,7-didehydro-4,5-á-epoxy-3,14-dihydroxyindolo[2',3':6,7]morphinan ditrifluoroacetate dihydrate.

A specific compound of the present invention is 7'-N'-cyano-N-[17-(cyclopropylmethyl)-6,7-didehydro-4,5á-epoxy-3,14-dihydroxyindolo[2',3':6,7]morphinian]-guanidine.

A specific compound of the present invention is 7'-N-cyano-N'-[3-(dimethylaminopropyl)]-N"-[17-(cyclopropylmethyl)-6,7-didehydro-4,5á-epoxy-3,14-dihydroxyindolo[2',3':6,7]morphinian]-guanidine.

A specific compound of the present invention is 7'-N-cyano-N'-[2-(1-aminoethylpyrrolidine)]-N"-[17-(cyclopropylmethyl)-6,7-didehydro-4,5á-epoxy-3,14-dihydroxyindolo[2',3':6,7]morphinian]-guanidine.

The invention also provides processes and intermediates useful for preparing compounds of formula (I) and formula (II) such as those described in the Examples or illustrated in the figures herein.

The compounds of general formula (I) and formula (II), or salts or solvates thereof, maybe prepared by the methods illustrated in schemes 1–6 (FIGS. 1 and 2), or by modification thereof, using readily available starting materials, reagents and conventional synthetic procedures.

The compounds of general formula (I) and formula (II) wherein X is NH can be readily synthesized by reaction of a 4,5-epoxy-6-ketomorphinan such as naltrexone (8, $R_1$=cyclopropylmethyl=CPM, $R_2$=OH, $R_3$=H, scheme 1) with a substituted phenyl hydrazine 9 under Fischer indolization conditions (see D. L. Hughes. *Org. Prep. Proc. Intl.* 25(6), 607–632, 1993). The indolomorphinan products 10 are subsequently reduced to the primary amines 11 by utilizing the reduction conditions set out in FIG. 1 (Scheme 1).

Guanidinyl compounds of general formula 12 (FIG. 2, scheme 2) can be prepared from amines 11 (where n=0–3) by reaction with a modified thiourea derivative 13 using mercuric(II)chloride assisted guanidylation protocols (see K. Y. Kim; L. Qian. *Tet. Lett.* 1993, 34, 48, 7677–7680 and M. A. Poss; E. Iwanowicz; J. A. Reid; J. Lin; Z. Gu. *Tet. Lett.* 33, 40, 5933–5936, 1992) followed by acid deprotection. 5'-GNTI ($R_1$=cyclopropylmethyl=CPM, $R_2$=OH, $R_3$=H, X=NH, $R_4$=NH, $R_5$=NH, $R_6$=H as its trifluoroacetate salt, general formula (I)) or more specifically 5'-guanidinyl-17-cyclopropylmethyl-6,7-didehydro-4,5-á-epoxy-3,14-dihydroxyindolo[2',3':6,7]-morphinan ditrifluoroacetate dihydrate is a specific example of this class.

Figure 4:
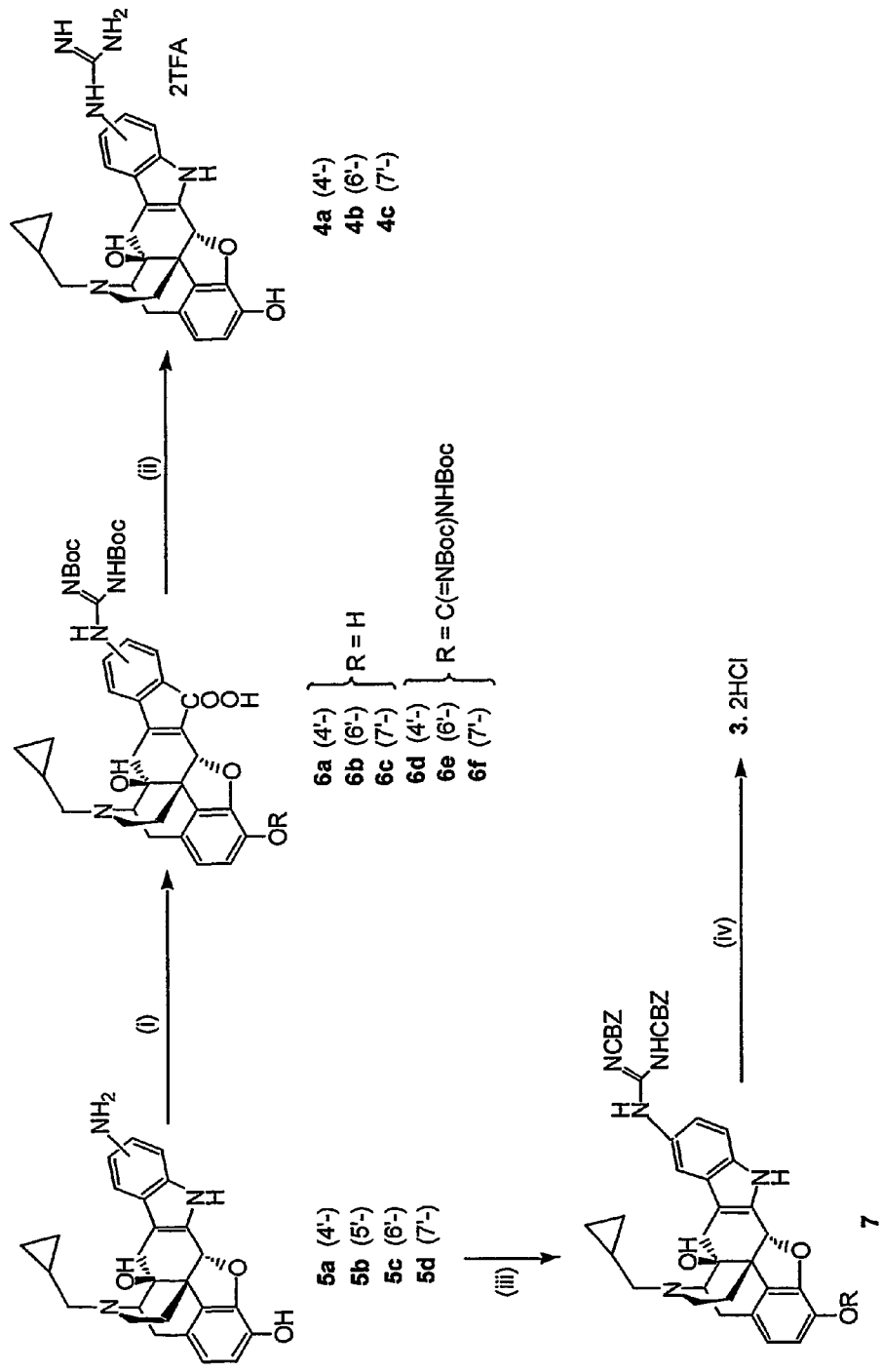
FIG. 4 Illustrates the synthesis of compounds 3, 4a, 4b, and 4c.

Applicant has also discovered a method for preparing multi-gram quantities of the kappa antagonist GNTI 3 as well as the other guanidino substituted compounds disclosed herein, which eliminates the need for tedious chromatographic separation. As illustrated in FIG. 4, 5'-Amino-NTI compound 5b was reacted with 3.3 equivalent of di-N',N"-carboxybenzyloxy-N'"-trifluoromethanesulfonyl-guanidine, see Konrad, F.; Zapf, C.; Sings, H. L.; Goodman, M. Diprotected Trifly-Guanidines: A New Class of Guanidinylation Reagents. *J. Org. Chem.*, 1998, 63, 3804–3805, in the presence of triethylamine in dichloromethane for 4 days to give bis(benzyloxycarbonyl)-protected intermediate 7. This intermediate 7 can also be prepared by the reaction of 5'-amino-NTI compound 5b with 1,3-bis(benzyloxycarbonyl)-2-methyl-2-thiopseudourea using the $HgCl_2$-assisted coupling reaction, see supra *Tetrahedron Lett.* 1993, 34, 7677–7680, *Tetrahedron Lett.* 1992, 33, 5933–5936, and *J. Med. Chem.* 2000, 43, 2362–2370. Deprotection of intermediate 7 was accomplished by catalytic hydrogenation with 10% Pd/C to afford compound 3.HCl. The overall yield from compound 5b by either of the modified routes was from about 65 to about 70 percent.

Thus, the invention provides a method for preparing a guanidino compound of formula (V):

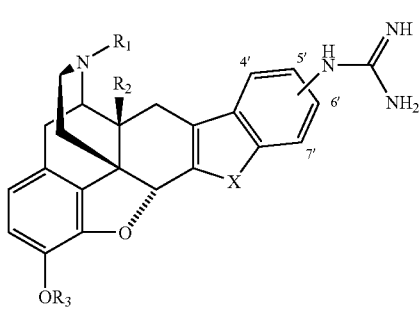

comprising converting the corresponding amine of formula (III):

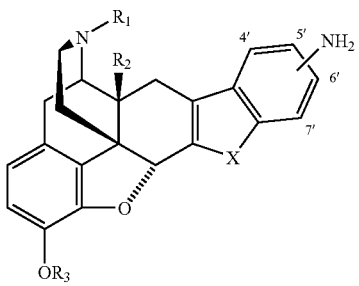

to a bisprotected compound of formula (IV);

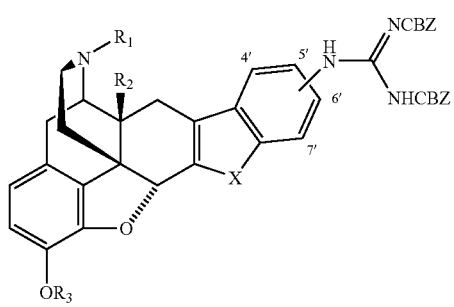

and deprotecting the compound of formula (IV) to provide the compound of formula (V).

The conversion of the amine of formula (III) to the bisprotected compound of formula (IV) can conveniently be carried out by reacting the amine with an excess (e.g. 2–10 equivalents) of di-N',N"-carboxybenzyloxy-N'"-trifluoromethanesulfonylguanidine, in the presence of a suitable base (e.g. a hindered amine base such as triethylamine) in a suitable solvent (e.g. a halogenated hydrocarbon such as $CH_2Cl_2$).

The deprotection of the compound of formula (IV) to provide the compound of formula (V) can conveniently be carried out by catalytic hydrogenation (e.g. with 10% Pd/C).

Cyanoguanidines of general formula 15 (FIG. 2, scheme 3) maybe obtained from amines 11 by reaction with diphenyl-N-cyanocarbonimidate 14 (see C. J. Durant et al. *J. Med. Chem.* 1977, 20, 7, 901 and R. L. Webb, C. S. Labaw. *J. Het. Chem.* 19, 1205, 1982) followed by displacement of phenol from the intermediate by reaction with a primary amine or general formula $R_6NH_2$. 5'-CNGNTI ($R_1$=cyclopropylmethyl=CPM, $R_2$=OH, $R_3$=H, X=NH, $R_4$=NCN, $R_5$=NH, $R_6$=H, general formula (I)) or more specifically 5'-N-cyanoguanidinyl-17-cyclopropylmethyl-6,7-didehydro-4,5-á-epoxy-3,14-dihydroxyindolo[2',3':6,7]-morphinan is a specific example of this class.

Ureas of general formula 16 (FIG. 2, scheme 4) wherein W is O or S can be readily prepared by reaction of amines 11 with $R_6NCW$. Specific variants of the above are cited in reaction scheme 5. Commercially available modified isothiocyanates of general formula 18 (n=0–3) (Fluka) are reacted with amines 11. Deprotection of the terminal tert-BOC moiety followed by guanidylation (see K. Y. Kim; L. Qian. *Tet. Lett.* 1993, 34, 48, 7677–7680 and M. A. Poss; E. Iwanowicz; J. A. Reid; J. Lin; Z. Gu. *Tet. Lett.* 33, 40, 5933–5936, 1992) and a second acid mediated tert-BOC deprotection yields compounds of general formula 17.

Figure 2:
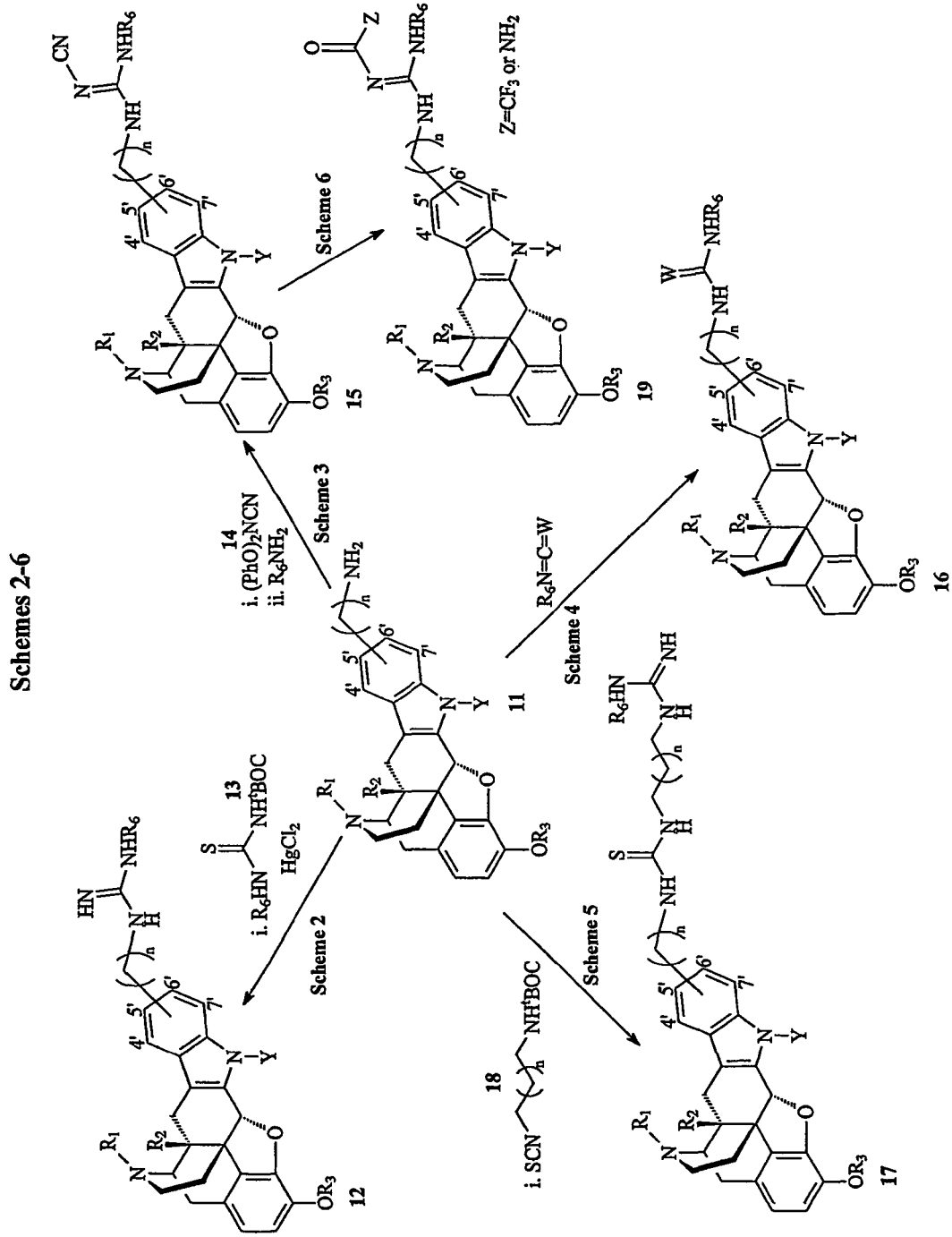
FIG. 2 Illustrates the synthesis of compounds of the invention.
Figure 3:
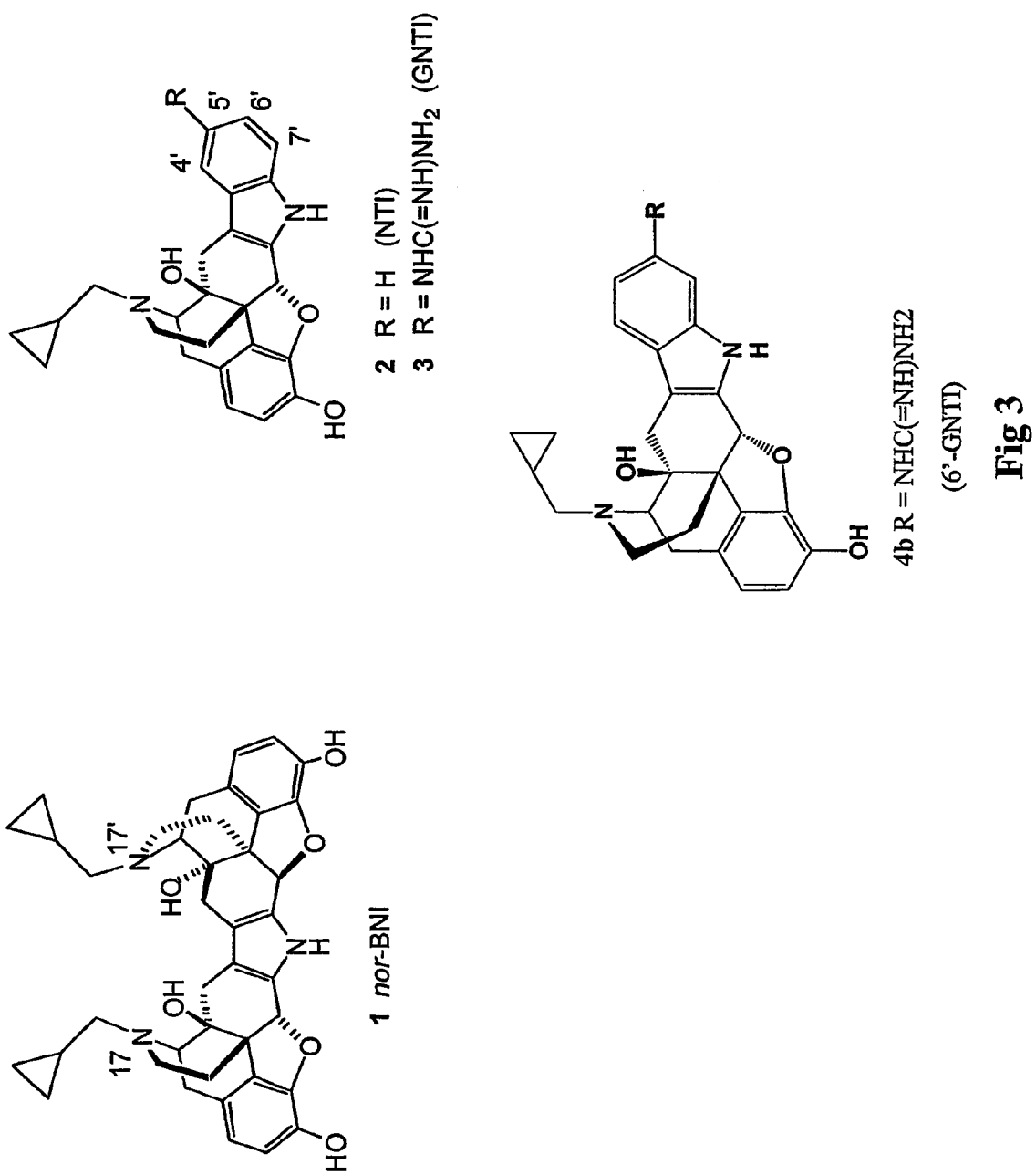
FIG. 3 Illustrates the structure of compound 4b (6'-GNTI) and related comparative compounds 1–3.

Cyanoguanidines 15 maybe modified further as depicted in FIG. 2, scheme 6 to afford compounds of general formula 19 (see S. N. Thorn. *Tet.* vol 49, 31, 6885, 1993). Compounds of formula (I) wherein X is O or S can be prepared from intermediates structurally similar to 11 wherein NY has been replaced by O or S. These intermediates can be prepared as generally disclosed in U.S. Pat. No. 4,816,586, which is incorporated by reference herein, which also discloses methods suitable for the preparation of salts of compounds of general formula (I) and (II).

4,5-Epoxy-6-ketomorphinans of general structure 8 (FIG. 1, scheme 1) can be prepared by synthetic methods which are well known in the art of organic chemistry (see U.S. Pat. No. 5,457,208 and citations therein).

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, á-ketoglutarate, and á-glycerophosphate.

Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula (I) and formula (II) can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula (I) to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula (I) and formula (II) can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose can be, for example, in the range of from about 0.01 to about 10 mg/kg, e.g., preferably from about 0.05 to about 1.0 mg/kg of body weight per day, most preferably in the range of 0.1 to 0.5 mg/kg/day.

The compounds of formula (I) and (II) can conveniently administered, for example, in unit dosage form; for example, containing 1 to 50 mg, conveniently 2 to 20 mg, most conveniently, 5 to 15 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The activity of a compound of the invention at the kappa opioid receptor can be determined using pharmacological models that are well known to the art, or using the procedures described below.

µ/κ selectivity ratios of 718 and 188, respectively. The 4'-regioisomer compound 4a was virtually inactive at all opioid receptor types. While the 7'-regioisomer compound 4c was inactive at mu and kappa-receptors, it was a potent delta opioid receptor antagonist.

TABLE 1

Opioid Antagonist Potency of GNTI Regioisomers in Smooth Muscle Preparations

| Compound | EK (κ)[a,c] | | DADLE (δ)[b,c] | | M (µ)[a,c] | |
|---|---|---|---|---|---|---|
| | $K_e$ (nM) | $IC_{50}$ ratio[d] | $K_e$ (nM) | $IC_{50}$ ratio[d] | $K_e$ (nM) | $IC_{50}$ ratio[d] |
| 1 (norBNI) | 0.41 | 49.8 ± 7.8 (10)[e] | 10.6 | 10.4 ± 2.9 (3) | 12.5 | 2.6 ± 0.6 (12)[e] |
| 3 | 0.16 | 139 ± 33 (11)[e] | 115 | 1.9 ± 0.5 (3) | 30.3 | 4.3 ± 0.7 (5) |
| 4a | 80 | 2.3 (2) | 263 | 1.4 (2) | f | 0.34 (2) |
| 4b | g | g | f | 0.2 (2) | g | g |
| 4c | 100 | 2.0 (2) | 0.96 | 105 ± 30 (4) | 238 | 1.4 ± 0.9 (3) |

[a]Determined in the guinea-pig-ileum (GPI) preparation.
[b]Determined in the mouse vas-deferens (MVD) preparation.
[c]All antagonists were tested at a concentration of 100 nM unless otherwise noted.
[d]Values are expressed mean ± standard error of the mean with the number of determinations in parentheses. The agonists employed were ethylketazocine (EK), morphine (M), [D-Ala²-D-leu⁵] enkephalin (DADLE).
[e]Tested at 20 nM.
[f]Not calculated because $IC_{50}$ ratio < 1.
[g]Not determined due to full agonist activity.

Smooth Muscle Preparations. The in vitro pharmacological data for GNTI 3 and compounds 4a–c, as well as the standard kappa antagonist, norBNI 1, are listed in Table 1. All of the compounds were tested on the electrically stimulated guinea-pig ileal longitudinal muscle (GPI), see Rang, H. P. Stimulant Actions of Volatile Anaesthetics on Smooth Muscle. *Br. J. Pharmacol.* 1964, 22, 356–365, and the mouse vas-deferens (MVD), see Henderson, G.; Hughes, J.; Kosterlitz, H. W. A New Example of a Morphine-Sensitive Neuroeffector Junction: Adrenergic Transmission in the Mouse vas Deferens. *Br. J. Pharmacol.* 1972, 46, 764–766, preparations for their agonist and antagonist activities as previously described, see (a) Portoghese, P. S.; Lipkowski, A. W.; Takemori, A. E. Binaltorphimine and Nor-binaltorphimine, Potent and Selective Kappa-Opioid Receptor Antagonists. *Life Sci.* 1987, 40, 1287–1292. (b) Portoghese, P. S.; Takemori, A. E. TENA. A Selective Kappa Opioid Receptor Antagonist. *Life Sci.* 1985, 36, 801–805. The compounds were incubated with the preparations 15 minutes prior to testing with standard selective agonists. Morphine (M), (−)-ethylketazocine (EK), and [D-Ala²,D-Leu⁵]enkephalin (DADLE) were employed as mu, kappa and delta selective agonists, respectively. Morphine and EK were used in the GPI, and DADLE was employed in the MVD studies. Concentration-response curves were obtained in the absence (control) and presence of the antagonist in the same preparation. Antagonist potency is expressed as an $IC_{50}$ ratio, that is the $IC_{50}$ of the agonist in the presence of antagonist divided by the control $IC_{50}$ of the agonist in the same preparation, and as a $K_e$ value derived from the relationship, $K_e$=[antagonist]/(1-$IC_{50}$ ratio).

Figure 5:
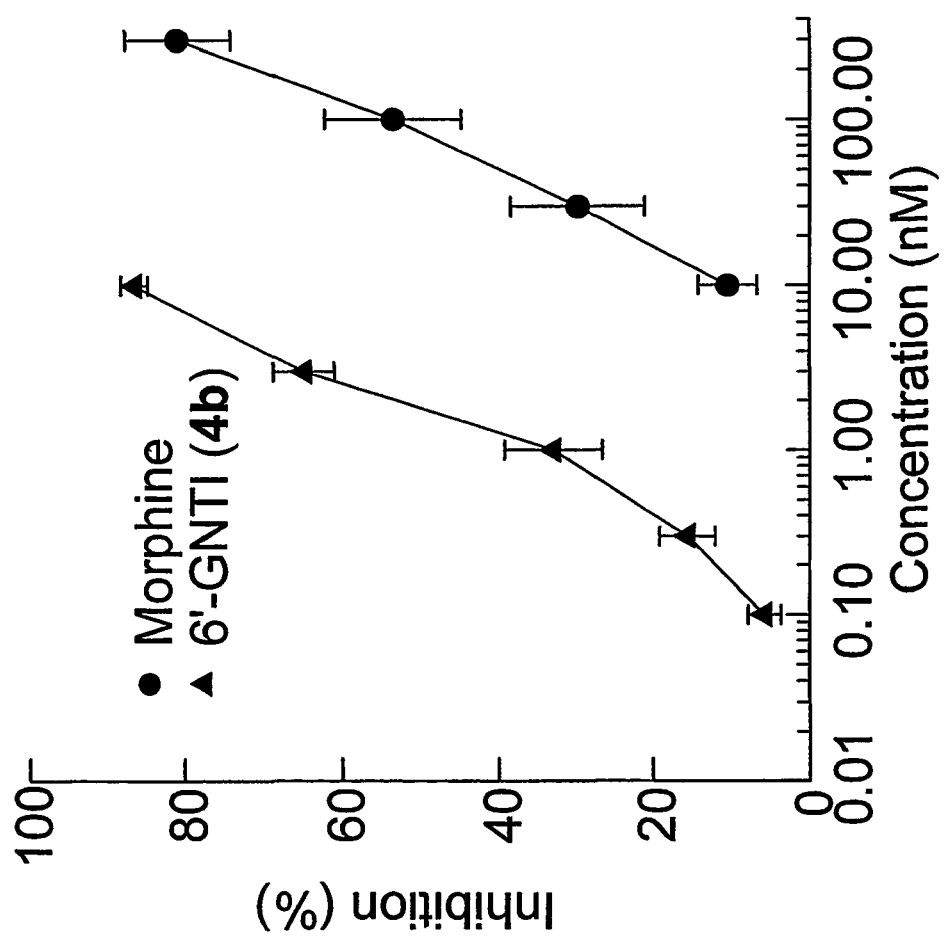
FIG. 5 Illustrates comparative concentration-response curves of compound 4b compared to morphine in a guinea-pig ileal preparation.

The data in Table 1 illustrates that the 5'-regioisomer GNTI compound 3 is a highly potent and selective kappa opioid receptor antagonist. In this regard GNTI was approximately four-fold more potent than norBNI 1, with δ/κ and GPI Assay Surprisingly, the 6'-regioisomer compound 4b was found to be an agonist with a 51-fold greater potency relative to that of morphine, reference FIG. 5 in the GPI assay. The finding that the agonist effect of compound 4b was only partially reversed by naltrexone (500 nM) suggested that it was not a mu-selective agonist. However, the kappa-selective antagonist, norBNI (20 nM), completely reversed the agonist effect. In MVD assay, compound 4b was inactive as an agonist at 1 µM and did not antagonize DADLE ($IC_{50}$ ratio=0.2). These results strongly suggest that compound 4b is a kappa-selective agonist.

Receptor Binding. HEK-293 in DMEM (Gibco, BRL) supplemented with 10% Bovine Calf Serum (Hyclone) and 1% penicillin/streptomycin (Gibco, BRL) were maintained at 37° C. and in 5% $CO_2$. Cells were seeded at 16% for 24 hours prior to transfection. Fresh media was added 2 hours prior to transfection. Cells were transfected with plasmid DNA (20 µg/100 mm plate) of either wild type or mutant receptor cDNA using the calcium phosphate precipitation method, see Chen, C.; Okayama, H. High Efficiency Transformation of Mammalian Cells by Plasmid DNA. *Mol. Cell. Bio.* 1987, 7, 2745–2752. Media was changed 5 hours after transfection. Transfected cells were harvested 48–72 hours after transfection for binding studies.

Sixty to 72 hours after transfection, HEK cells were washed three times with 25 mM HEPES buffer (pH 7.4) and were resuspended with 8–12 mL of 25 mM HEPES/100 mm plate. Saturation binding assays were performed in triplicate. Nonselective binding was determined using 10 µM naltrexone. Assays were incubated at room temperature for 90 minutes in a total binding volume of 0.5 mL and were terminated by filtration through a Whatman GF/B filter that had been presoaked in 0.25% poly(ethyleneimine) immediately prior to filtration. Filters were washed three times with 4 mL of ice-cold 25 mM HEPES buffer, and scintillation counting was performed with a Beckman 3801 LS Scintillation Counter. Protein concentrations were determined by the method of Bradford, see Bradford, M. M. A Rapid and Selective Method for the Quantitation of Microgram Quantities of Protein utilizing the Principle of Protein-dye Binding. *Anal. Biochem.* 1976, 72, 248–254. Raw binding data was analyzed with RADLIG and LIGAND (G. A. McPherson, Biosoft, Cambridge, UK). Inhibition constants ($K_i$) were determined from $IC_{50}$ values with the Cheng-Prusoff equation, see Cheng, Y. C.; Prusoff, W. H.; Relationship between the inhibition Constant ($K_i$) and the concentration of inhibitor which causes 50 per cent inhibition ($I_{50}$) of an enzymatic reaction. *Biochem. Pharmacol.* 1973, 22, 3099–3108.

As summarized in Table 2, receptor binding was determined in triplicate using [$^3$H]diprenorphine on HEK-293 cells that were transiently transfected with plasmids encoding rat kappa-, rat mu-, or mouse delta-opioid receptors. GNTI 3 possessed greater than two orders of magnitude higher affinity for the kappa receptor relative to mu and delta receptors. Consistent with the smooth muscle data, substitution at the 4'-position (compound 4a) eliminated binding to all three receptor types. Like GNTI, the 6'-regioisomer compound 4b was kappa-selective, but possessed one-tenth the affinity of GNTI for kappa receptors. The results are consistent with the kappa agonist selectivity of compound 4b observed in the GPI. The delta selectivity of regioisomer compound 4c also corresponded well with the functional data. Binding to mu receptors was uniformly low for all regioisomers.

TABLE 2

Binding Affinity to Cloned Opioid Receptors

| Compound | $K_i$ (nM) | | |
|---|---|---|---|
| | κ | δ | μ |
| 3 | 0.14 ± 0.03 | 24.8 ± 11.3 | 99.7 ± 8.7 |
| 4a | >1000 | >1000 | >1000 |
| 4b | 1.15 ± 0.39 | 20.3 ± 6.7 | 81.8 ± 20.7 |
| 4c | 69.1 ± 25 | 2.75 ± 0.48 | 181 ± 20 |

General. Materials. Naltrexone was obtained from Mallinckrodt & Co. All reactions were carried out under an inert atmosphere of nitrogen. Triethylamine ($NEt_3$) was distilled from KOH, while dichloromethane and acetonitrile were distilled from calcium hydride prior to their use. Dry dimethyformamide (DMF) was obtained by storing reagent grade material over 3 Å sieves for at least 24 h. All other chemicals were either HPLC or reagent grade and used without further purification. Thin layer chromatography (TLC) was performed on analytical Uniplate silica gel GF plates (250 μm by 2.5×20 cm) and preparative thin layer chromatography on 1.0 or 0.5 mm silica gel plates purchased from Analtech. Gravity and low pressure column chromatography were performed over silica gel (200–400 mesh, 60 Å, Aldrich) as the stationary phase under $N_2$. The reverse phase high pressure liquid chromatography (HPLC) was performed with Beckman model 110A pumps, a Beckman Analytical Optical Unit (fixed wavelength UV), and a Hewlett-Packard HP 3390A integrating recorder. Purifications were performed with a Ranin Dynamax macro HPLC column (C18, 5 μm, 1×28 cm) or an Alltech Altima C18 column (10 μm, 250×22 mm). Chromatographic elution solvent systems are reported as vol:vol ratios. Infrared (IR) spectra were recorded on a Perkin-Elmer PE-281 spectrophotometer or a Nicolet 5DXC FT-IR spectrometer as potassium bromide (KBr) disks. Low resolution (LRMS) and high resolution (HRMS) mass spectra were obtained on a Finnigan 4000 or VG-707EHF spectrometer by the Chemistry Mass Spectrometry Laboratory at the Department of Chemistry, University of Minnesota. All $^1$H and $^{13}$C spectra were recorded on a Varian 300-MHz or a GE 300-MHz spectrometer, and the chemical shifts are reported as δ values with units of parts-per-million (ppm). $^1$H NMR spectra are referenced to tetramethylsilane (TMS) at 0.00 ppm as an internal standard and $^{13}$C NMR spectra are referenced to either $CDCl_3$ (77.00 ppm), or DMSO-$d_6$ (40.00 ppm) and are recorded at room temperature (20±1° C.). All recorded spectra are for the free base unless otherwise stated. Elemental analyses were performed by M-H-W Laboratory in Phoenix, Ariz. and are within ±0.4% of theoretical values. Melting points were determined in open capillary tubes on a Thomas-Hoover melting point apparatus and are uncorrected. All of the tested regioisomer of GNTI (compounds 3, 4a–c) were purified by silica gel flash chromatography ($CH_2Cl_2$—MeOH—$NH_4OH$, 78:20:2), then by silica gel preparative TLC ($CH_2Cl_2$—MeOH—$NH_4OH$, 78:20:2), and finally by reverse-phase HPLC ($CH_3CN$—$H_2O$, 65:35 containing 0.1% of TFA), to afford as their TFA salts.

The invention will be further illustrated by the following non-limiting Examples.

EXAMPLE 1

4'-N'-(N'',N'''-Bis(tert-butoxycarbonyl)guanidino-17-(cyclopropylmethyl)-6,7-didehydro-4,5α-epoxy-3,14-hydroxyindolo-[2',3':6,7]morphinian (6a).

In a 250 mL flask, a mixture of compound 5a (325 mg, 0.75 mmol) and $HgCl_2$ (400 mg, 1.33 mmol) in HPLC grade $CH_2Cl_2$ (50 mL) was stirred for few minutes and added 1,3-bis(tert-butoxycarbonyl)-2-methyl-2-thiopseudourea (320 mg, 1.1 mmol) followed by few drops of $NEt_3$. The mixture was allowed to stir at room temperature under a sealed $N_2$ atmosphere. The progress of the reaction was monitored by TLC. After completion the reaction (24 hours), mixture was filtered through Celite under vacuum to remove mercuric sulfide, and the residue was washed thoroughly with methanol. The combined filtrate was concentrated to give a solid product which was subjected to column chromatography ($CH_2Cl_2$—MeOH—$NH_4OH$, 94.5:5.0:0.5) to give two products. The major product was compound 6a (410 mg, 79%): mp 255° C. (dec); $^1$H NMR (DMSO-$d_6$): δ 11.57 (s, 1H, NH), 11.33 (s, 1H, NH), 10.00 (s, 1H, NH), 8.93 (s, 1H, Ar—OH), 7.17–7.11 (m, 2H, ArH), 7.09–6.97 (m, 1H, ArH), 6.46 (m, 2H, ArH), 5.46 (s, 1H, 5-H), 4.70 (b, 1H, 14-OH), 3.24–3.02 (m, 1H), 2.84–2.79 (m, 1H), 2.64–2.59 (m, 2H), 2.45–2.38 (m, 1H), 2.36 (m, 2H), 2.27–2.25 (m, 2H), 2.16–2.12 (m, 1H), 1.49 (s, 9H, $^t$Bu), 1.27 (s, 9H, $^t$Bu), 0.99 (m, 1H), 0.45 (m, 2H), 0.09 (m, 2H); HRMS (FAB) m/z 672.3386 (M+H)$^+$, $C_{37}H_{45}N_5O_7$ requires 671.3397. The minor product was compound 6d (26 mg, 3.8%): mp>280° C.; $^1$H NMR (DMSO-$d_6$): δ 11.46 (s, 1H, NH), 11.22 (s, 1H, NH), 10.70 (s, 1H, NH), 9.83 (s, 1H, NH), 7.36 (s, 1H, ArH), 7.25 (d, 1H, J=8.1 Hz, ArH), 7.16 (d, 1H, J=8.1 Hz, ArH), 6.70 (d, 1H, J=8.1 Hz, ArH), 6.66 (d, 1H, J=8.4 Hz, ArH), 5.61 (s, 1H, 5-H), 4.76 (b, 1H, 14-OH), 3.14 (d, 1H, J=18.9 Hz), 2.81–2.63 (m, 5H), 2.39–2.46 (m, 3H), 2.12 (m, 1H), 1.53 (d, 1H, J=13.2 Hz), 1.47 (s, 9H, $^t$Bu), 1.38 (s, 9H, $^t$Bu), 1.31 (s, 9H, $^t$Bu), 1.25 (s, 9H, $^t$Bu), 0.84 (m, 1H), 0.47 (m, 2H), 0.12 (m, 2H). HRMS (FAB) m/z 914.4717 (M+H)$^+$, $C_{48}H_{63}N_7O_{11}$ requires 913.4585.

EXAMPLE 2

6-N'-(N'',N'''-Bis(tert-butoxycarbonyl)guanidino-17-(cyclopropylmethyl)-6,7-didehydro-4,5α-epoxy-3,14-hydroxyindolo-[2',3':6,7]morphinian (6b).

A mixture of compound 5c (216 mg, 0.5 mmol), HgCl$_2$ (250 mg, 0.83 mmol), 1,3-bis(tert-butoxycarbonyl)-2-methyl-2-thiopseudourea (200 mg, 0.7 mmol) in freshly dried CH$_2$Cl$_2$ containing few drops of NEt$_3$ was allowed to stir for 18 h under a sealed N$_2$ atmosphere at room temperature. After work up of the reaction according to the above procedure for compound 6a, it gave two products which were separated by column chromatography (CH$_2$Cl$_2$—MeOH—NH$_4$OH, 94.5:5.0:0.5); the major product was compound 6b (260 mg, 78%): mp 270° C. (dec); $^1$H NMR (DMSO-d$_6$): δ 11.43 (s, 1H, NH), 11.20 (s, 1H, NH), 10.00 (s, 1H, NH), 8.88 (s, 1H, Ar—OH), 7.69 (s, 1H, ArH), 7.25 (d, 1H, J=8.7 Hz, ArH), 6.90 (d, 1H, J=8.7 Hz, ArH), 6.47 (d, 1H, J=8.1 Hz, ArH), 6.42 (d, 1H, J=8.1 Hz, ArH), 5.44 (s, 1H, 5-H), 4.70 (b, 1H, 14-OH), 3.24–3.07 (m, 2H), 3.02 (m, 1H), 2.60 (m, 2H), 2.48–2.08 (m, 5H), 1.53 (m, 1H), 1.48 (s, 9H, $^t$Bu), 1.38 (s, 9H, $^t$Bu), 0.80 (m, 1H), 0.45 (m, 2H), 0.12 (m, 2H); $^{13}$C NMR (DMSO-d$_6$): δ 153.35, 152.81, 143.56, 140.31, 136.98, 131.64, 131.44, 130.87, 124.73, 124.24, 118.73, 117.37, 114.99, 110.56, 106.23, 84.34, 72.66, 62.11, 59.11, 47.74, 43.80, 39.15, 31.79, 29.18, 28.40, 23.14, 9.71, 4.35, 3.97. HRMS (FAB) m/z 672.3405 (M+H)$^+$, C$_{37}$H$_{45}$N$_5$O$_7$ requires 671.3397. The minor product was compound 6e (12 mg, 2.6%): mp>280° C.; $^1$H NMR (DMSO-d$_6$): δ 11.44 (s, 1H, NH), 11.28 (s, 1H, NH), 10.70 (s, 1H, NH), 10.02 (s, 1H, NH), 7.37 (s, 1H, ArH), 7.27 (d, 1H, J=7.8 Hz, ArH), 6.89 (d, 1H, J =8.1 Hz, ArH), 6.72 (d, 1H, J=8.4 Hz, ArH), 6.68 (d, 1H, J=8.1 Hz, ArH), 5.60 (s, 1H, 5-H), 4.76 (b, 1H, 14-OH), 3.12 (d, 1H, J=18.1 Hz), 2.78–2.56 (m, 3H), 2.48–2.36 (m, 5H), 2.16–2.03 (m, 1H), 1.52 (m, 1H), 1.49 (s, 9H, $^t$Bu), 1.36 (s, 18H, $^t$Bu), 1.26 (s, 9H, $^t$Bu), 0.86 (m, 1H), 0.47 (m, 2H), 0.12 (m, 2H); HRMS (FAB) m/z 914.4670 (M+H)$^+$, C$_{48}$H$_{63}$N$_7$O$_{11}$ requires 913.4585.

EXAMPLE 3

7'-N'-(N'',N'''-Bis(tert-butoxycarbonyl)guanidino-17-(cyclopropylmethyl)-6,7-didehydro-4,5α-epoxy-3,14-hydroxyindolo-[2',3':6,7]morphinian (6c).

A mixture of compound 5d (420 mg, 1 mmol), HgCl$_2$ (430 mg, 1.44 mmol), 1,3-bis(tert-butoxycarbonyl)-2-methyl-2-thiopseudourea (380 mg, 1.3 mmol), few drops of NEt$_3$ in dried CH$_2$Cl$_2$ was allowed to stir for 18 hour at room temperature under a sealed N$_2$ atmosphere and worked up according to the procedure for compound 6a. On subjecting the mixture to column chromatography (CH$_2$Cl$_2$—MeOH—NH$_4$OH, 94.5:5.0:0.5), it gave major product compound 6c (530 mg, 81%): mp 230° C. (dec); $^1$H NMR (DMSO-d$_6$): δ 11.64 (s, 1H, NH), 11.28 (s, 1H, NH), 9.67 (s, 1H, NH), 8.89 (s, 1H, Ar—OH), 7.26 (d, 1H, J=7.5 Hz, ArH), 6.97–6.89 (m, 2H, ArH), 6.50–6.43 (m, 2H, ArH), 5.70 (s, 1H, 5-H), 4.70 (b, 1H, 14-OH), 3.27 (m, 2H), 3.06 (d, 1H, J=18.3 Hz), 2.73–2.65 (m, 2H), 2.44–2.03 (m, 5H), 1.51 (s, 9H, $^t$Bu), 1.26 (s, 9H, $^t$Bu), 0.86 (m, 1H), 0.46 (m, 2H), 0.11 (m, 2H); $^{13}$C NMR (DMSO-d$_6$): δ 155.93, 143.54, 140.48, 133.38, 131.28, 130.74, 128.24, 124.52, 121.09, 118.95, 118.82, 117.98, 117.36, 111.11, 84.25, 72.72, 62.11, 59.02, 47.77, 43.89, 31.80, 29.29, 28.69, 28.31, 23.21, 9.52, 4.42, 3.95; HRMS (FAB) m/z 672.3406 (M+H)$^+$, C$_{37}$H$_{45}$N$_5$O$_7$ requires 671.3397; and the minor product compound 6f (34 mg, 3.7%): mp 165° C. (dec); $^1$H NMR (DMSO-d$_6$): δ 11.63 (s, 1H, NH), 11.37 (s, 1H, NH), 10.70 (s, 1H, NH), 9.66 (s, 1H, NH), 7.26 (d, 1H, J=8.1 Hz, ArH), 6.98 (d, 1H, J=6.60 Hz, ArH), 6.91 (d, 1H, J=7.5 Hz, ArH), 6.73 (d, 1H, J=8.1 Hz, ArH), 6.66 (d, 1H, J=7.2 Hz, ArH), 5.61 (s, 1H, 5-H), 4.70 (b, 1H, 14-OH), 3.44 (m, 1H), 3.39 (m, 1H), 3.14 (d, 1H, J=18.9 Hz), 2.85–2.68 (m, 3H), 2.45–2.29 (m, 4H), 2.18–2.13 (m, 1H), 1.51 (s, 9H, $^t$Bu), 1.37 (s, 9H, $^t$Bu), 1.32 (s, 9H, $^t$Bu), 1.30 (s, 9H, $^t$Bu), 0.88 (m, 1H), 0.49 (m, 2H), 0.12 (m, 2H); HRMS (FAB) m/z 914.4630 (M+H)$^+$, C$_{49}$H$_{63}$N$_7$O$_{11}$ requires 913.4585.

EXAMPLE 4

4'-Guanidino-17-(cyclopropylmethyl)-6,7-didehydro-4,5α-epoxy-3,14-hydroxyindolo-[2',3':6,7]morphinian (4a).

Compound 6a (400 mg, 0.6 mmol) was dissolved in HPLC grade CH$_2$Cl$_2$ and cooled the content in an ice-bath. TFA (3.0 mL) was added in divided portions over a period of 10 minutes and the flask was sealed under N$_2$ atmosphere and allowed to stir at room temperature. The reaction was monitored by TLC, and after 36 hours, CH$_2$Cl$_2$ and TFA were removed with a stream of N$_2$, leaving a residue which was subjected to column chromatography (CH$_2$Cl$_2$—MeOH—NH$_4$OH, 78:20:2) to afford compound 4a along with CF$_3$CO$_2$$^-$NH$_4$$^+$. Further purification was accomplished by preparative TLC (CH$_2$Cl$_2$—MeOH—NH$_4$OH, 78:20:2) to give compound 4a (211 mg, 75%); IR KBr disk υ (cm$^{-1}$): 3400–3150 (br), 1675 (s), 1507, 1463, 1432, 1332, 1202, 1134; $^1$H NMR (DMSO-d$_6$): δ 11.64 (s, 1H, NH), 9.84 (s, 1H, NH), 9.32 (s, 1H, NH), 8.92 (s, 1H, Ar—OH), 7.33–7.06 (m, 4H, ArH and NH$_2$), 6.78 (d, 1H, J=7.20 Hz, ArH), 6.59 (d, 1H, J=8.1 Hz, ArH), 6.52 (d, 1H, J=8.1 Hz, ArH), 5.64 (s, 1H, 5-H), 4.11 (b, 1H, 14-OH), 3.44 (m, 1H), 3.12–2.99 (m, 4H), 2.87 (m, 1H), 2.70–2.55 (m, 4H), 1.76 (d, 1H, J=11.7 Hz), 1.07 (m, 1H), 0.64–0.56 (m, 2H), 0.37–0.44 (m, 2H); HRMS (FAB) m/z 472.2357 (M+H)$^+$, C$_{27}$H$_{29}$N$_5$O$_3$ requires 471.2270

EXAMPLE 5

6'-Guanidino-17-(cyclopropylmethyl)-6,7-didehydro-4,5α-epoxy-3,14-hydroxyindolo-[2',3':6,7]morphinian (4b).

Compound 6b (500 mg, 0.75 mmol) was dissolved in a mixture of TFA (3.0 mL) and dried CH$_2$Cl$_2$ (28 mL) and allowed to stir under N$_2$ atmosphere at room temperature for 36 h. The reaction was worked up according to the procedure for compound 4a and purified by preparative TLC to give 4b (260 mg, 74%) as a free base; IR KBr disk υ (cm$^{-1}$): 3450–3150 (br), 1683 (s), 1506, 1463, 1433, 1330, 1202, 1132; $^1$H NMR (DMSO-d$_6$): δ 11.50 (s, 1H, NH), 9.96 (s, 1H, NH), 9.29 (s, 1H, NH), 8.95 (s, 1H, Ar—OH), 7.36–7.09 (m, 3H, ArH and NH$_2$), 6.77 (d, 1H, J=8.10 Hz, ArH), 6.59–6.52 (m, 2H, ArH), 6.39 (s, 1H), 5.67 (s, 1H, 5-H), 4.05 (b, 1H, 14-OH), 3.43–3.23 (m, 3H), 3.18–3.06 (m, 2H), 2.96–2.91 (m, 2H), 2.68–2.57 (m, 2H), 2.50 (m, 1H), 1.78 (d, 1H, J=11.7 Hz), 1.05 (m, 1H), 0.68 (m, 1H), 0.58 (m, 1H), 0.40 (m, 2H). HRMS (FAB) m/z 472.2356 (M+H)$^+$, C$_{27}$H$_{29}$N$_5$O$_3$ requires 471.2270.

EXAMPLE 6

7'-Guanidino-17-(cyclopropylmethyl)-6,7-didehydro-4,5α-epoxy-3,14-hydroxyindolo-[2',3':6,7]morphinian (4c).

Intermediate compound 6c (530 mg, 0.78 mmol), TFA (3 mL) and $CH_2Cl_2$ (28 mL) were subjected to conditions similar to that employed to the procedure for compound 4a to give compound 4c (251 mg, 67%) as a free base; IR KBr disk υ ($cm^{-1}$): 3450–3150 (br), 1676 (s), 1506, 1462, 1431, 1324, 1202, 1134; $^1$H NMR (DMSO-$d_6$): δ 11.65 (s, 1H, NH), 9.88 (s, 1H, NH), 9.31 (s, 1H, NH), 8.96 (s, 1H, Ar—OH), 7.34–7.03 (m, 4H, ArH and $NH_2$), 6.60 (d, 1H, J=8.10 Hz, ArH), 6.53 (d, 1H, J=8.7 Hz, ArH), 6.39 (s, 1H), 5.62 (s, 1H, 5-H), 4.07 (b, 1H, 14-OH), 3.43–3.23 (m, 4H), 3.18–3.06 (m, 2H), 2.98–2.90 (m, 2H), 2.67–2.52 (m, 2H), 1.78 (d, 1H, J=15.7 Hz), 1.05 (m, 1H), 0.68 (m, 1H), 0.59 (m, 1H), 0.41 (m, 2H); HRMS (FAB) m/z 472.2338 $(M+H)^+$, $C_{27}H_{29}N_5O_3$ requires 471.2270.

EXAMPLE 7

5'-N'-(N'',N'''-Bis(benzyloxycarbonyl)guanidino-17-(cyclopropylmethyl)-6,7-didehydro-4,5α-epoxy-3, 14-hydroxyindolo-[2',3':6,7]-morphinian (7).

Method-A. A mixture of N,N'-di-carboxybenzyloxy-N''-trifluoromethanesulfonylguanidine (380 mg, mmol, 3.3 eqv.), 5'-amino-NTI 5b (1.06 g, 2.5 mmol) and triethylamine (1.5 mL) in dry $CH_2Cl_2$ (50 mL) was stirred at room temperature until all of compound 5b was consumed as measured by TLC. After completion of the reaction (4 days), the mixture was diluted with $CH_2Cl_2$ (100 mL), and washed with 2M of sodium bisulfate, saturated $NaHCO_3$, and brine. After drying with $MgSO_4$ and filtering, the solvent was removed under reduced pressure and the crude product was subjected to flash column chromatography on silica gel ($CH_2Cl_2$—MeOH—$NH_4OH$, 94.5:5.0:0.5) to give 1.41 g (76%) of compound 7.

Method-B. 5'-Amino-NTI 5b (2.68 g, 6.24 mmol) was dissolved in freshly distilled dry $CH_2Cl_2$ and added 3.0 mL of triethylamine. To this mixture, $HgCl_2$ (2.70 g, 10 mmol) was added followed by 1,3-bis(benzyloxycarbonyl)-2-methyl-2-pseudothiourea (2.64 g, 7.33 mmol) in portion. The flask was sealed under $N_2$ atmosphere and allowed to stir at room temperature and the progress of the reaction was monitored by TLC ($CH_2Cl_2$—MeOH—$NH_4OH$, 89:10:1). After completion of the reaction (2 hours), it was filtered through Celite under vacuum to remove $HgSO_4$ and the residue was washed thoroughly with methanol. The combined filtrate were concentrated under reduced pressure to give brownish material which was subjected to column chromatography ($CH_2Cl_2$—MeOH—$NH_4OH$, 97.5:2.0:0.5) to give compound 7 (3.84 g, 78%); $^1$H NMR (DMSO-$d_6$): δ 11.35 (s, 1H, NH), 11.09 (s, 1H, NH), 9.83 (s, 1H, NH), 8.82 (s, 1H, 3-OH), 7.38 (s, 1H, Ar), 7.16–7.04 (m, 13H), 7.01 (m, 1H, ArH), 6.38–6.31 (m, 2H), 5.62 (s, 1H), 5.08 (b, 2H), 4.93 (b, 2H), 4.62 (b, 1H, 14-OH), 3.34–3.24 (m, 1H), 3.01 (d, 1H, J=19.2 Hz), 2.70–2.56 (m, 2H), 2.46–2.24 (m, 4H), 2.21 (m, 1H), 1.54 (d, 1H, J=11.1 Hz), 0.86 (m, 1H), 0.48 (m, 2H), 0.12 (m, 2H). $^{13}$C NMR (DMSO-$d_6$): δ 153.78, 143.79, 143.59, 135.40, 131.77, 131.58, 129.10, 128.84, 128.73, 128.49, 127.31, 127.11, 126.73, 124.92, 119.30, 119.02, 117.67, 113.98, 112.04, 110.93, 84.53, 72.85, 63.66, 62.39, 59.30, 55.60, 48.04, 43.98, 31.83, 29.36, 23.31, 9.87, 4.54, 4.22. HRMS (FAB) m/z 740.3093 $(M+H)^+$, $C_{43}H_{41}N_5O_7$ requires 739.8355.

EXAMPLE 8

5'-Guanidino-17-(cyclopropylmethyl)-6,7-didehydro-4,5α-epoxy-3,14-hydroxyindolo-[2',3':6,7]morphinian Hydrochloride (3. 2HCl).

Di-Cbz-protected GNTI 7 (820 mg, 1.10 mmol) was dissolved in MeOH (100 mL). To a Parr hydrogenating bottle, 100 mg of Pd/C (10% by weight) was added and followed by anhydrous MeOH, care was taken to avoid a fire and as a precaution a nitrogen atmosphere can be used in the bottle. Di-Cbz-protected GNTI solution was added to the reaction bottle, stirred well and added dilute HCl drop wise. The reaction bottle was subjected to hydrogenation at a pressure of 65 psi. After completion of the reaction (4 hours), it was left overnight at room temperature. The soluble part was decanted and the residue was stirred two times with 150 mL of hot MeOH (containing 5% of water) for a few minutes and filtered off. The combined filtrate were concentrated to a volume of about 5 mL under reduced pressure. Lyophilization gave the dihydrochloride salt of compound 3 (520 mg, 90%); 3. 2HCl: IR KBr disk υ ($cm^{-1}$): 3400–3200 (br), 1675 (s), 1502, 1461, 1430, 1325, 1202, 1136; $^1$H NMR (DMSO-$d_6$): δ 11.56 (s, 1H, NH), 9.92 (s, 1H, NH), 9.35 (s, 1H, NH), 9.00 (s, 1H, 3-OH), 7.40–7.33 (m, 3H, $NH_2$), 7.15 (s, 1H, ArH), 6.90 (d, 1H, J=8.10 Hz, ArH), 6.87 (d, 1H, J=5.7 Hz, ArH), 6.64–6.50 (m, 2H, ArH), 5.68 (s, 1H, 5-H), 4.14 (d, 1H, J=5.7 Hz, 14-OH), 3.43 (m, 1H), 3.26 (m, 1H), 3.16–3.06 (m, 2H), 2.94–2.90 (m, 2H), 2.69–2.57 (m, 2H), 2.54–2.45 (m, 2H), 1.77 (d, 1H, J=15.7 Hz), 1.10 (m, 1H), 0.71–0.66 (m, 1H), 0.63–0.59 (m, 1H), 0.50–0.47 (m, 1H), 0.43–0.39 (m, 1H).

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:
1. A compound of formula (I):

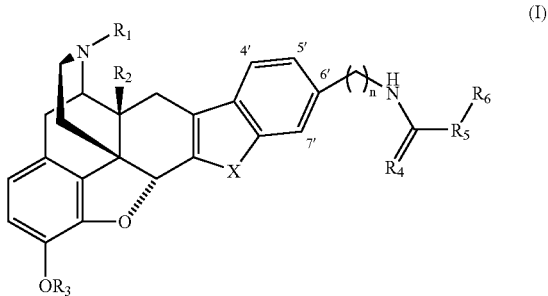

wherein
R$_1$ is ($C_1$–$C_6$)alkyl, ($C_2$–$C_6$)alkenyl, ($C_2$–$C_6$)alkynyl, ($C_3$–$C_7$)cycloalkyl, ($C_5$–$C_7$)cycloalkenyl, ($C_3$–$C_6$)cycloalkyl($C_1$–$C_6$)alkyl, ($C_5$–$C_7$)cycloalkenyl($C_1$–$C_6$) alkyl, aryl, heteroaryl, aryl($C_1$–$C_6$)alkyl, or heteroaryl ($C_1$–$C_6$)alkyl;

R$_2$ is H, OH, ($C_1$–$C_6$)alkoxy, ($C_1$–$C_6$)alkanoyloxy, NR$_a$R$_b$ or SR$_c$;

R₃ is H, aryl(C₁–C₆)alkyl, (C₁–C₆)alkyl, (C₁–C₆)alkanoyl, or (C₁–C₆)alkylC(=S);

R₄ is =O, =S, or =N$R_d$;

$R_d$ is H, CN, CONH₂, COCF₃, (C₁–C₆)alkanoyl, (C₁–C₆)alkyl, or (CH₂)$_p$NR$_e$R$_f$; or $R_d$ together with R₆ is —(CH₂)$_q$— and forms a ring;

p is 1, 2, 3, or 4;

R₅ is NR$_m$;

R₆ is H, (C₁–C₆)alkyl, (C₃–C₇)cycloalkyl, aryl, heteroaryl, aryl(C₁–C₆)alkyl, heteroaryl(C₁–C₆)alkyl, NR$_g$R$_h$(C₁–C₆)alkyl, or C(=NR$_j$)NHR$_k$; or when R₄ is =NR$_d$, R₆ together with R$_d$ is —(CH₂)$_q$— and forms a ring;

q is 2 or 3;

X is O, S, or NY;

Y is H, (C₁–C₆)alkyl, or aryl(C₁–C₆)alkyl;

n is 0, 1, 2, 3, or 4;

R$_a$–R$_c$ and R$_e$–R$_f$ are each independently H, (C₁–C₆)alkyl, (C₁–C₆)alkanoyl, or —C(=S)(C₁–C₆)alkyl;

R$_g$ and R$_h$ are each independently H, (C₁–C₆)alkyl, (C₁–C₆)alkanoyl, —C(=NH)NR$_a$R$_b$, or —C(=S)(C₁–C₆)alkyl, or R$_g$ and R$_h$ together with the nitrogen to which they are attached are pyrrolidino, piperidino or morpholino;

R$_j$ and R$_k$ are each independently H, (C₁–C₆)alkyl, (C₂–C₆)alkenyl, (C₂–C₆)alkynyl, (C₃–C₇)cycloalkyl, (C₃–C₇)cycloalkyl(C₁–C₆)alkyl, (C₅–C₇)cycloalkenylalkyl, aryl, heteroaryl, aryl(C₁–C₆)alkyl, or heteroaryl(C₁–C₆)alkyl; and R$_m$ is hydrogen or (C₁–C₆)alkyl;

or a pharmaceutically acceptable salt thereof.

2. The compound of claim 1 wherein R₁ is (C₂–C₆)alkenyl or (C₃–C₆)cycloalkyl(C₁–C₆)alkyl.

3. The compound of claim 1 wherein R₁ is cyclopropylmethyl or allyl.

4. The compound of claim 1 wherein R₂ is OH.

5. The compound of claim 1 wherein R₃ is H.

6. The compound of claim 1 therein R₄ is =NR$_d$.

7. The compound of claim 1 therein R₄ is =NH or =NCN.

8. The compound of claim 1 therein R₅ is NH.

9. The compound of claim 1 therein R₆ is H.

10. The compound of claim 1 therein R₆ is hydrogen, ethyl, n-butyl, 3-(dimethylamino)propyl, or 2-pyrrolidinoethyl.

11. The compound of claim 1 wherein R₆ is C(=NR$_j$)NHR$_k$.

12. The compound of claim 1 wherein R$_d$, together with R₆, is —(CH₂)$_q$— and forms a ring.

13. The compound of claim 1 wherein R$_m$ is hydrogen.

14. The compound of claim 1 wherein n is 0.

15. The compound of claim 1 wherein n is 1.

16. The compound of claim 1 wherein X is NH.

17. The compound of claim 1 wherein R₁ is cyclopropylmethyl; R₂ is hydroxy; R₃ is H; R₄ is =NH; R₅ is NH; and R₆ is H.

18. A composition comprising a compound of claim 1, and a pharmaceutically acceptable diluent or carrier.

19. A therapeutic method for treating a pathological condition or symptom in a mammal wherein kappa receptor activity is implicated and agonism of kappa receptors is desired comprising administering to the mammal an effective amount of a compound of claim 1 wherein the condition or symptom is pain.

* * * * *